(12) United States Patent
Jarząb et al.

(10) Patent No.: US 9,890,194 B2
(45) Date of Patent: Feb. 13, 2018

(54) EPITOPE AND ITS USE

(71) Applicant: WROCLAWSKIE CENTRUM BADAŃEIT+ SP. Z O.O., Wroclaw (PL)

(72) Inventors: Anna Ewelina Jarząb, Brzeg Dolny (PL); Danuta Witkowska, Wroclaw (PL); Edmund Ziomek, Wroclaw (PL); Andrzej Gamian, Wroclaw (PL)

(73) Assignee: WROCLAWSKIE CENTRUM BADAN EIT+ SP. Z O.O., Wroclaw (PL)

( * ) Notice: Subject to any disclaimer, the term of this patent is extended or adjusted under 35 U.S.C. 154(b) by 0 days.

(21) Appl. No.: 14/441,248

(22) PCT Filed: Nov. 7, 2013

(86) PCT No.: PCT/PL2013/050026
§ 371 (c)(1),
(2) Date: May 7, 2015

(87) PCT Pub. No.: WO2014/073998
PCT Pub. Date: May 15, 2014

(65) Prior Publication Data
US 2016/0024150 A1 Jan. 28, 2016

(30) Foreign Application Priority Data
Nov. 7, 2012 (PL) .................................... P.401502

(51) Int. Cl.
*C07K 7/06* (2006.01)
*G01N 33/569* (2006.01)

(52) U.S. Cl.
CPC ......... *C07K 7/06* (2013.01); *G01N 33/56916* (2013.01)

(58) Field of Classification Search
CPC ..................................................... C07K 7/06
See application file for complete search history.

(56) References Cited

U.S. PATENT DOCUMENTS

| | | | | |
|---|---|---|---|---|
| 2005/0196397 | A1* | 9/2005 | Scheiflinger | C07K 16/40 424/145.1 |
| 2006/0122377 | A1* | 6/2006 | Dennis | C07K 16/2845 530/387.3 |
| 2009/0144849 | A1* | 6/2009 | Lutfiyya | C07K 14/415 800/278 |
| 2009/0220991 | A1* | 9/2009 | Polakiewicz | C07K 16/18 435/7.8 |
| 2010/0047170 | A1* | 2/2010 | Denmeade | A61K 47/48338 424/9.1 |
| 2010/0069293 | A1* | 3/2010 | Bolotin | A61K 47/60 514/17.5 |
| 2010/0291096 | A1* | 11/2010 | Schroeder | C07K 14/005 424/139.1 |
| 2010/0297066 | A1* | 11/2010 | Stopek | A61K 9/0024 424/85.2 |
| 2011/0038888 | A1* | 2/2011 | Emtage | A61K 9/0014 424/192.1 |
| 2012/0065131 | A1* | 3/2012 | Dake | A61K 8/64 514/12.1 |
| 2012/0088695 | A1* | 4/2012 | Fang | C12N 5/0068 506/26 |
| 2013/0330335 | A1* | 12/2013 | Bremel | G06F 19/18 424/134.1 |

FOREIGN PATENT DOCUMENTS

| WO | 2008/004902 A2 | | 1/2008 | |
|---|---|---|---|---|
| WO | WO 2013/040142 | * | 3/2013 | ........... A61K 39/395 |

OTHER PUBLICATIONS

Wei, J. (Infection and Immunity 71(5), 2775-2786, 2003).*
Haiyan Zhao et al., "The host outer membrand proteins OmpA and OmpC are associated with teh Shigella phage Sf6 virion," Virology, vol. 49, pp. 319-327 (2011).

* cited by examiner

*Primary Examiner* — Amber D Steele
(74) *Attorney, Agent, or Firm* — Arrigo, Lee & Guttman LLP

(57) ABSTRACT

An isolated protein containing a common epitope recognized by umbilical blood antibodies specific against enterobacteria, occurring in an extract of bacterial outer membrane proteins, and fragments thereof containing said common epitope, which can be used in medicine and pharmaceutics, particularly in the production of vaccines and diagnostic tests as well as affinity materials.

6 Claims, 3 Drawing Sheets

Fig. 1

Fig. 2

EPITOPE AND ITS USE

SEQUENCE LISTING

Figure 3:
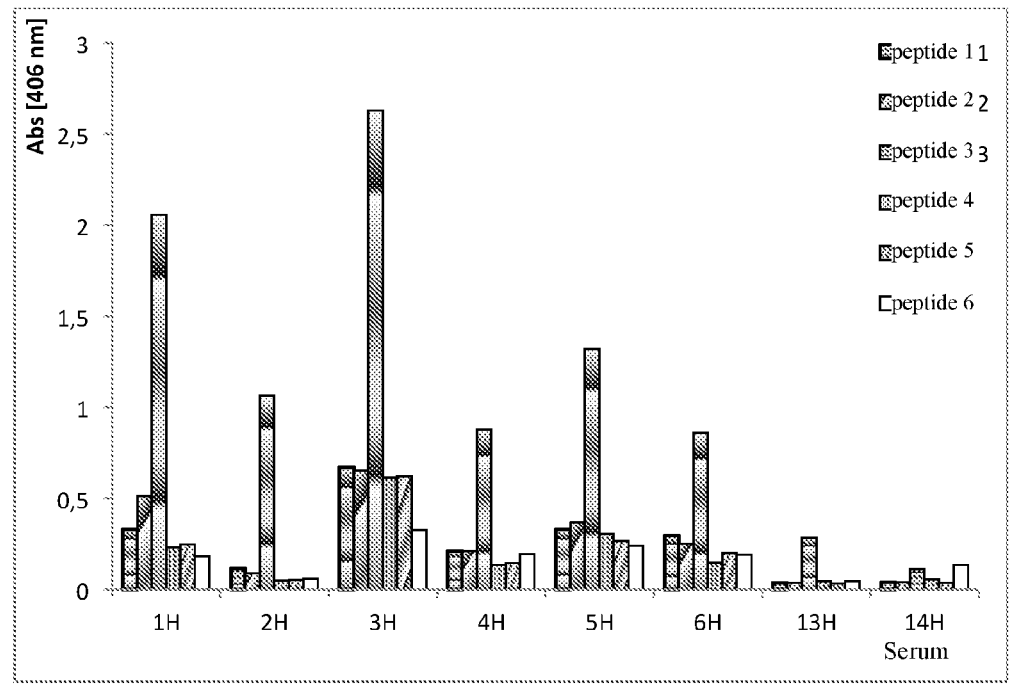

The instant application contains a Sequence Listing which has been submitted electronically in ASCII format and is hereby incorporated by reference in its entirety. Said ASCII copy, created on Oct. 12, 2015, is named PZ-1722-RW-US_SL.txt and is 18,372 bytes in size.

The subject of the present invention is an epitope recognized by umbilical blood antibodies specific against enterobacteria, which may be used in the production of vaccines against *Enterobacteriaceae*, particularly opportunistic gastrointestinal bacterial pathogens, particularly bacteria of the genus *Shigella*.

Shigellosis, *salmonellosis* and other diseases caused by members of the family *Enterobacteriaceae*are still a considerable medical problem, particularly in developing nations.

The genus *Shigella* belongs to Gram-negative opportunistic human pathogens and is responsible for colonic infections. Symptoms of infection include lower abdominal pain, fever and bloody diarrhoea which may cause a life threatening dehydration. Bacterial diarrhoea is in third place world wide in terms of causes of juvenile mortality below the age of five years. Infant and child mortality due to bacterial infections are generally caused by low standards of sanitation pervasive in developing nations. Nevertheless, infections by pathogenic intestinal bacteria, including *Shigella*, also occur in developed nations. Here, a bigger problem consists of strains resistant to antibiotics. For this reason, healthcare authorities both in developing and developed nations are pushing for prevention, including vaccination. Thus far, no one has managed to produce a vaccine against opportunistic bacterial pathogens of the gastrointestinal tract. For approval, such a vaccine must fulfil a series of criteria, such as activity in intestinal mucosa, long-term immune protection and a lack of adverse effects. It is also desirable that the vaccine be easy to administer and relatively inexpensive, because children in nations with poor economies will constitute the major recipient.

*Shigella* strains against which it has been attempted to produce vaccines include *S. flexneri* 2a, 3a, *S. dysenteriae* 1, and *S. sonnei*.

Application P.380105 discloses a protein of the external cell wall of *Shigella flexneri* 3a with a molecular mass of 38 kDa which is immunoreactive with human serum. The application suggests, amongst others, its possible use as a carrier for use in conjugate vaccines.

The goal of the present invention is to obtain novel components which could be used to produce a vaccine against *Enterobacteriaceae*, particularly against opportunistic pathogens of the gastrointestinal tract, particularly against bacteria of the genus *Shigella*.

The subject of the present invention is an epitope with the following amino-acid sequence: A1-A2-A3-A4-A5-A6 (SEQ ID NO: 1), where:

A1denotes R,
A2denotes Y,
A3denotes D, R, E, N or Q,
A4denotes E, D, N or Q,
A5denotes R,
A6denotes Y, G or F.

Preferably, an epitope according to the present invention has been selected from a group encompassing peptides with the following amino-acid sequence: RYDERY (SEQ ID NO: 2), RYDDRY (SEQ ID NO: 3), RYEERY (SEQ ID NO: 4), RYQERY (SEQ ID NO: 5) or RYDQRY (SEQ ID NO: 6).

The next subject of the present invention is the use of the epitope defined above or a protein containing this epitope in the production of a vaccine against *Enterobacteriaceae*, particularly those against bacteria of the genus *Shigella*.

The next subject of the present invention is the use of an epitope defined above or a protein containing this epitope in the production of a diagnostic test for detecting antibodies against *Enterobacteriaceae*, particularly bacteria of the genus *Shigella*.

The next subject of the present invention is the use of the epitope defined above or a protein containing such an epitope in the production of blood-derived, immunoglobulin therapeutic preparations specific against *Enterobacteriaceae*, particularly bacteria of the genus *Shigella*.

Unexpectedly, using to the peptides according to the present invention, it is possible to replace a classic vaccine based on thermally attenuated bacteria with a vaccine based on synthetic fragments representing the main surface antigen of bacterial cells isolated from the ompC protein. In contrast to the classic vaccine, the synthetic vaccine is safe, inexpensive and may be produced on a mass scale.

The disclosed peptides can be used to construct a vaccine against *Enterobacteriaceae*, particularly in cases of humoral immunity insufficiencies. They may also be used to prepare an affinity gel for the isolation of antibodies from donor sera as a therapeutic preparation, and for the diagnosis of specific humoral immunity insufficiencies. In contrast to the native ompC protein, which contains a series of superfluous, neutral or even negative epitopes, an epitope according to the present invention contains only a unique protective property.

To facilitate a better understanding of the nature of the present invention, its description has been illustrated with the following figures:

Figures 1, 2:
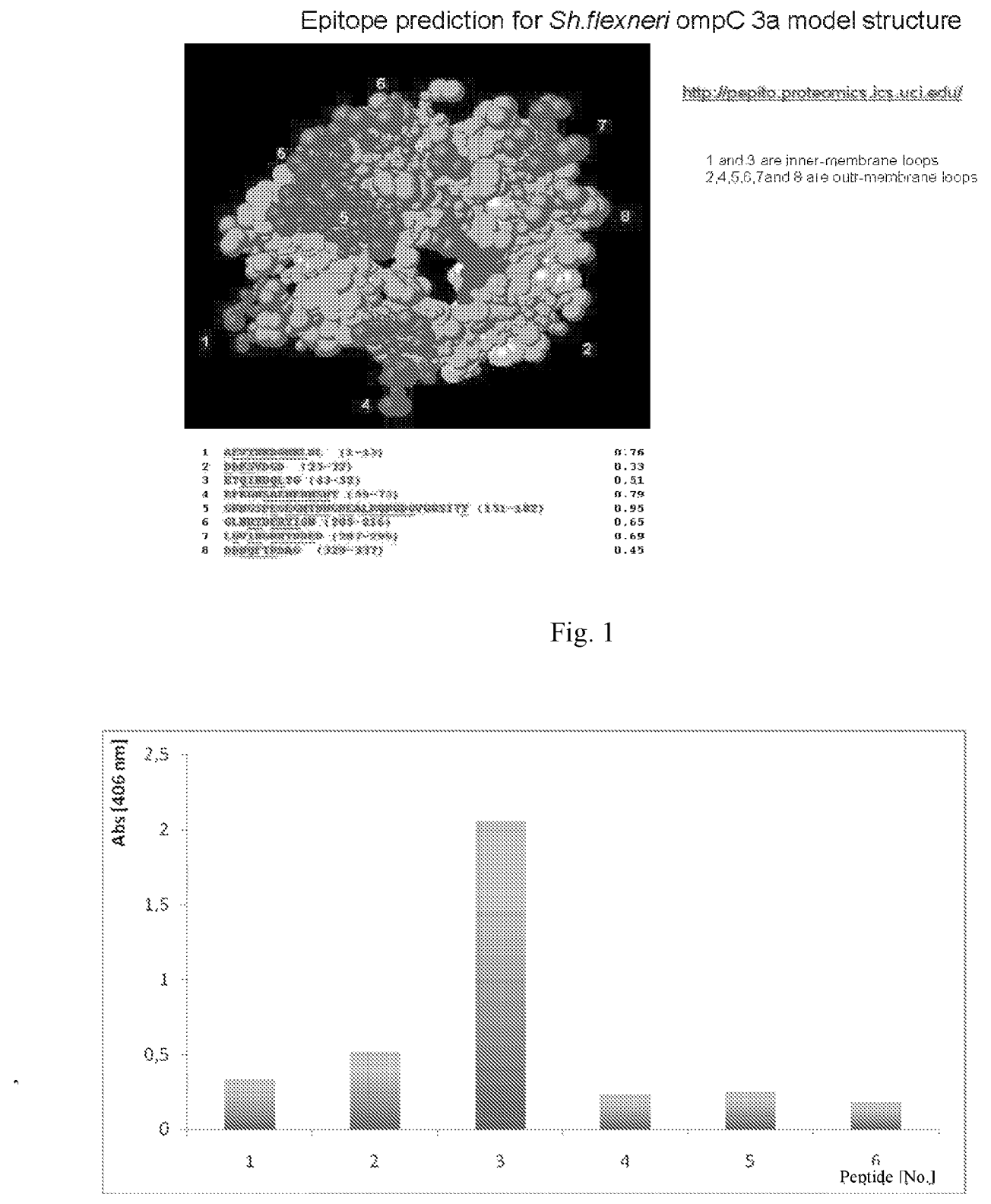

FIG. 1 represents a visualisation of conformational epitopes from the ompC protein of *Shigella flexneri* 3a. Epitopes 1-3 (SEQ ID NOS 47-49, respectively, in order of appearance) are loops directed to the interior of the cell, and for this reason are of lesser significance to host-bacteria interactions. Epitopes 4-8 (SEQ ID NOS 50-53 and 11, respectively, in order of appearance) correspond to extracellular loops II-VI respectively (according to the nomenclature of ompC of *E. coli*).

FIG. 2 represents the observed reactivity of antibodies present in sera 1H-9H mixed with peptides Nos. 1-6 synthesized on HPM-pins.

FIG. 3 represents the reactivity of antibodies present in the individual sera 1H-6H and 13H-14H with peptides Nos. 1-6 synthesized on HPM-pins.

FIG. 4 represents amino-acids that determine the immunological activity of the RYDERY epitope (SEQ ID NO: 2) of ompC (SEQ ID NO: 54).

FIG. 5 represents the activities of peptides derived from the RYDERY peptide (SEQ ID NO: 2), in regard to antibodies present in human umbilical blood sera (SEQ ID NOS 2, 55-60, 2, 61-66, 2, 67-70, 3-4, 71, 2, 5-6 and 72-75, respectively, in order of appearance).

FIG. 6 represents the level of anti-OMP-38 class IgG antibodies in murine sera following immunization with poly-lysine conjugates, OMP-38 protein, as well as nonimmunized mice, and determined using an ELISA test (SEQ ID NOS 41 and 44-46, respectively, in order of appearance).

EXAMPLE 1

Production of an Extract of Bacterial Outer Membrane Proteins (OMP)

A fresh bacterial mass from a 7-hour culture on liquid BHI medium at a temperature of 37° C. was obtained by centrifugation and rinsed with 10 mM Tris-HCl buffer pH 7,6 containing 10 mM $MgSO_4$. The bacteria were suspended in the same buffer with an addition of 20 µg RNase and 20 µg DNase per ml and sonified for 10 min. The disrupted bacteria were centrifuged at 7000×g to remove undisrupted cells, and then the resulting supernatant was ultracentrifuged at 150000×g for 1 hour to remove envelope fragments. To dissolve the cell membrane, the ultracentrifuged precipitate was extracted twice at room temperature with 10 mM Tris-HCl, pH 7,6 containing 10 mM $MgSO_4$ and 2% Triton X-100. After centrifugation at 150000×g the resulting precipitate was extracted twice with the same buffer containing 2% Triton X-100 and 5 mM EDTA and centrifuged at 160000×g. The outer membrane proteins dissolved in the supernatant were precipitated with two volumes of 95% ethanol and characterised using PAGE. OMP fractions contained around 20 proteins, and contained no more than 5% lipopolysaccharide, which was determined based on Kdo content.

EXAMPLE 2

Preparation of a 38 kDa Protein Immunoreactive with Human Serum

The preparative electrophoresis of outer membrane proteins was preferably conducted using a Prep Cell 491 apparatus from BioRad using a 37 mm column, which was loaded with 80 ml of 10% or 12.5% separating gel and 20 ml 5% of stacking gel with a buffer containing 25 mM Tris, 0.192 mM glycine and 1% SDS, pH 8.3 was used for electrophoresis and elution. After loading 30-40 mg of protein extract on the stacking gel, electrophoresis was performed at 260 V and 109 mA. Elution was initiated when the dye, bromophenol blue, exited the separating gel. During the elution, we collected fractions of 1.4 ml, and the presence of protein in the fractions was monitored at a wavelength of 280 nm with a UV detector and verified via electrophoresis and immunoblotting. Fractions with appropriate proteins, preferably 38 kDa, were dialysed into water, pooled and concentrated through centrifugation under a vacuum. OMP fractions were characterised in a polyacrylamide gel under reducing conditions using 10% or 12.5% gels and standard methods.

EXAMPLE 3

Sequence Determination of the Protein Temporarily Denoted as omp38 and Establishment of its Homology to a Protein Known as ompC The ompC sequence was determined at the protein and DNA levels. We isolated and purified omp38 from *Shigella flexneri* 3a as described above. The purified protein was hydrolysed with trypsin and the resulting fragments were analysed using mass spectrometry (ESI-MS/MS). In this way, we determined 67% of the ompC sequence. This was confirmed and completed following the isolation of the ompC gene and DNA sequence determination. We determined that ompC of *Shigella flexneri* 3a has an identical sequence to that determined for ompC of *Shigella flexneri* 2a (GeneBank, AE014073.1), *Shigella boydii* Sb227 (GeneBank CP000036.1), *Shigella flexneri* 5 (GeneBank CP000266.1) and *Shigella flexneri* 2002017 (GeneBank CP001383.1).

EXAMPLE 4

Construction of a 3-dimensional Model of ompC of *Shigella flexneri* 3a Based on the Structure of Homologous Proteins Available from the PDB Database In order to build a 3D model of the *Shigella flexneri* 3a ompC sequence, we threaded the ompC of *E. coli* into the structure using a method available from the internet at http://swissmodel.expasy.org [Arnold K., Bordoli L., Kopp J., and Schwede T., The SWISS-MODEL Workspace: A web-based environment for protein structure homology modelling, Bioinformatics, 2006, 22, 195-201]. The resulting antigen model was subjected to a PEPITO bioinformatic analysis simulating which amino-acids may interact with antibodies [Sweredoski, M. J. and Baldi, P., Bioinformatics Application Note, 2008, 24, 12, 1459-1460]. This method is also available on the Internet (http://pepito.proteomics.ics.uci.edu).

FIG. 1 shows the resulting visualisation of the conformational epitopes.

EXAMPLE 5

Synthesis of Peptides Representing Five (5) Bioinformatically Predicted Potential Epitopic Regions and Determination that Only One of them, Loop V, Reacts with Umbilical Serum Based on the bioinformatic analysis, we designed the syntheses of five peptides corresponding to extracellular epitopic regions. These were:

1. GNSAENENNSWT-pin        (62-73)    (SEQ ID NO: 7)
2. EGEGMTNNGREALRQNGDGV-pin (157-176) (SEQ ID NO: 8)
3. GLNRYDERYIGN-pin        (205-216)  (SEQ ID NO: 9)
4. GVINGRNTDDED-pin        (287-299)  (SEQ ID NO: 10)
5. DDNQFTRDAG-pin          (327-336)  (SEQ ID NO: 11)

Peptides representing the bioinformatically predicted regions were synthesized using an NCP kit with 96 hydroxypropylmethacrylate (HPM) pins (MIMOTOPES, Clayton, Victoria, Australia) according to the manufacturer's specifications (Carter, J.M. (1994) An epitope mapping of a protein using the Geysen (PEPSCAN) procedure. Methods Mol Biol 36: 207-223). As the sixth, control, peptide we synthesised a fragment corresponding to the N-terminal region of ompC (AEVYNKDGNKLD-pin (SEQ ID NO: 12)).

After the completed synthesis, we performed initial reactivity tests for the individual peptides, using a standard ELISA test. The ELISA was performed in a mixture of 9 different umbilical blood sera (1H-9H) according to the following scheme:

a. Pin equilibration in TBS-T.
b. Blocking of free sites on the pins using 1% BSA in TBS-T
c. Incubation with umbilical sera at a dilution of 1:500 in a solution of 1% BSA in TBS-T buffer
d. Rinsing with TBS-T buffer
e. Incubation with secondary antibodies, conjugated Anti-Human IgG (Fc)-AP (Promega)
f. Rinsing with TBS-T
g. Reaction of AP with the substrate pNPP (p-Nitrophenyl Phosphate, Sigma) and absorbance measurement at 405 nm
h. Dissociation of proteins/antibodies from peptides synthesized on HPM-pins.

The results obtained are presented in FIG. 2.

Only peptide No. 3, representing a looped region of the ompC protein (loop V) found between amino-acids 205-216 (GLNRYDERYIGN (SEQ ID NO: 9)) turned out to be active immunologically.

We also determined the individual reactivity of umbilical blood sera from various patients (1H-6H, 13H, 14H) against peptides (nr 1-6) synthesized on HPM-pins. The results obtained (FIG. 3) confirmed the earlier result (FIG. 2) which identified peptide No. 3 as the most reactive. They also indicate individual differences at the level of antibodies recognizing peptide No. 3 in different patients.

EXAMPLE 6

Establishment of the Minimal Length of the Immunologically Active Peptide Representing Loop V The next stage of research meant to demonstrate the sequence of the epitope binding antibodies present in umbilical blood serum was the determination of the full and minimal sequence of the epitope which guarantees antibody binding. For this reason we performed a chemical synthesis of short peptides representing sequences in the region of loop V. We synthesized 29 different twelve amino-acid peptides, which overlapped by one amino-acid. These are shown in Table 1.

TABLE 1

Sequences of peptides representing loop V of ompC responsible for the reaction with umbilical blood.

| N-end | | | | | | | | | | | | C-end-(HPM-pin) | SEQ ID NO: |
|---|---|---|---|---|---|---|---|---|---|---|---|---|---|
| 1 | R | A | E | T | Y | T | G | G | L | K | Y | D | 13 |
| 2 | D | R | A | E | T | Y | T | G | G | L | K | Y | 14 |
| 3 | G | D | R | A | E | T | Y | T | G | G | L | K | 15 |
| 4 | N | G | D | R | A | E | T | Y | T | G | G | L | 16 |
| 5 | G | N | G | D | R | A | E | T | Y | T | G | G | 17 |
| 6 | I | G | N | G | D | R | A | E | T | Y | T | G | 18 |
| 7 | Y | I | G | N | G | D | R | A | E | T | Y | T | 19 |
| 8 | R | Y | I | G | N | G | D | R | A | E | T | Y | 20 |
| 9 | E | R | Y | I | G | N | G | D | R | A | E | T | 21 |
| 10 | D | E | R | Y | I | G | N | G | D | R | A | E | 22 |
| 11 | Y | D | E | R | Y | I | G | N | G | D | R | A | 23 |
| 12 | R | Y | D | E | R | Y | I | G | N | G | D | R | 24 |
| 13 | N | R | Y | D | E | R | Y | I | G | N | G | D | 25 |
| 14 | L | N | R | Y | D | E | R | Y | I | G | N | G | 26 |
| 15 | G | L | N | R | Y | D | E | R | Y | I | G | N | 9 |
| 16 | F | G | L | N | R | Y | D | E | R | Y | I | G | 27 |
| 17 | N | F | G | L | N | R | Y | D | E | R | Y | I | 28 |
| 18 | Q | N | F | G | L | N | R | Y | D | E | R | Y | 29 |
| 19 | D | Q | N | F | G | L | N | R | Y | D | E | R | 30 |
| 20 | D | D | Q | N | F | G | L | N | R | Y | D | E | 31 |
| 21 | T | D | D | Q | N | F | G | L | N | R | Y | D | 32 |
| 22 | R | T | D | D | Q | N | F | G | L | N | R | Y | 33 |
| 23 | K | R | T | D | D | Q | N | F | G | L | N | R | 34 |
| 24 | S | K | R | T | D | D | Q | N | F | G | L | N | 35 |
| 25 | S | S | K | R | T | D | D | Q | N | F | G | L | 36 |
| 26 | S | S | S | K | R | T | D | D | Q | N | F | G | 37 |
| 27 | V | S | S | S | K | R | T | D | D | Q | N | F | 38 |
| 28 | A | V | S | S | S | K | R | T | D | D | Q | N | 39 |
| 29 | A | A | V | S | S | S | K | R | T | D | D | Q | 40 |

To exclude the possibility of non-specific interactions, the control consisted of HPM-pins blocked solely with glycine residues. No non-specific antibody binding to HPM-pins were noted.

The ELISA assay conducted on a mixture of umbilical sera 1H-9H demonstrated that peptides denoted with numbers 12-18 (Table 1) are responsible for binding antibodies in these sera. From the immunological sequence analysis of the active peptide it stems that the common element for this series of sequences is the sequence RYDERY (SEQ ID NO: 2). This peptide also turned out to be the shortest active portion of the epitope.

EXAMPLE 7

Figure 4:
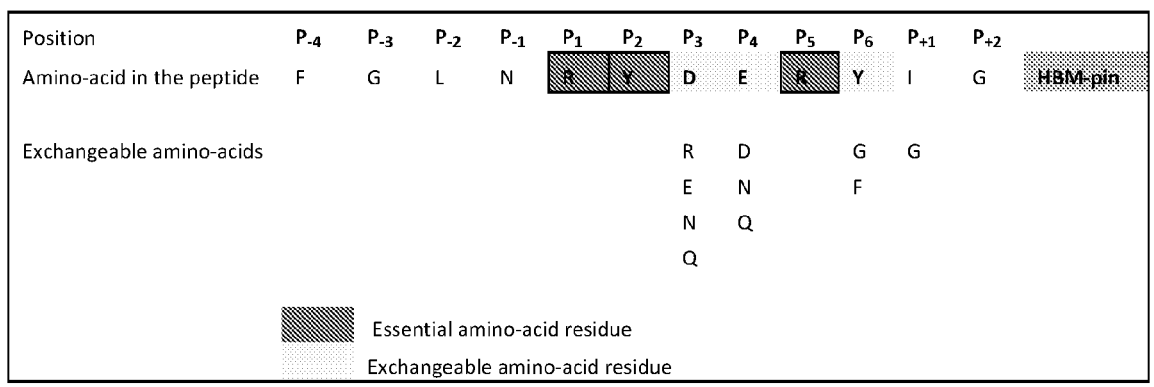

Determination of Critical and Less Significant Amino-acid Positions for Immunological Activity in the Minimal Peptide RYDERY (SEQ ID NO: 2). Optimization of the Peptide Sequence Unexpectedly it was shown that the immunological activity of the RYDERY peptide (SEQ ID NO: 2) is not affected by the removal of amino-acids in positions $P_{+1}$ and $P_{+2}$, nor in $P_{-1}$, $R_{-2}$, $P_{-3}$ and $R_{-4}$. The removal of amino-acids in positions $P_1$ or $P_6$, and in the subsequent positions ($P_2$, $P_3$ or $P_5$, $P_4$) caused a complete loss of activity. Likewise, a loss of immunological activity was caused by an exchange of residues at positions $P_1$, $P_2$ and $P_5$. The latter amino-acids must remain unchanged in the final form of the peptide vaccine. Positions $P_3$, $P_4$ and $P_6$ are less restrictive. In this case native amino-acids may be substituted by a series of other residues without any significant loss of immunological activity (FIG. 4). This property of the epitope facilitates the synthesis of a peptide less susceptible to enzymatic hydrolysis, and a higher antigenicity.

Figure 5:
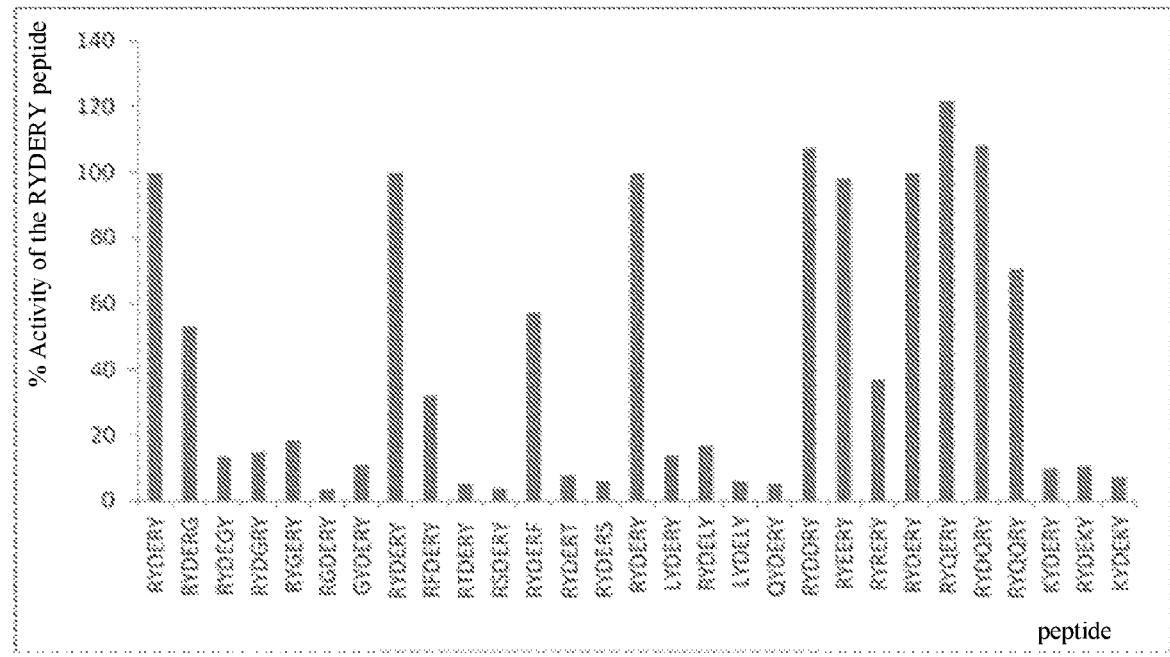

Furthermore, it was unexpectedly shown that an alteration of amino-acid D or E for Q yields an increased reactivity with umbilical serum (FIG. 5).

EXAMPLE 8

Setting the Immunologically Active Peptide on Carriers Such as Polymers and Proteins One of the commonly accepted methods of preparing an artificial antigen is the synthesis of an immunologically active peptide on a resin with previously synthesised and attached poly-lysine. Such a carrier makes it possible to attach eight peptide chains. The resulting synthetic antigen has a molecular mass of about 9 kDa.

We prepared 5 different conjugates differing in terms of peptide sequences synthesized thereon. Four contained the sequence RYDERYIG (SEQ ID NO: 41) (the IG residues occur in the natural protein sequence and were used as linkers facilitating a better exposition of the peptide by separating it from the poly-Lys carrier) and were successively elongated using N, LN, GLN amino-acid residues (from the natural ompC protein sequence and exhibiting antigenicity with regard to class IgG antibodies from umbilical blood sera). One such conjugate, containing the YDERY sequence (SEQ ID NO: 42), which demonstrated no activity in earlier experiments may constitute a control.

The series of the above mentioned artificial antigens was synthesized (Table 2) and used to immunize mice.

It is also possible to use natural proteins as antigen peptides (haptens) carriers. Typical carrier proteins are bovine serum albumin (BSA), keyhole limpet hemocyanin (KLH) and ovalbumin (OVA) (see; *Bioconjug Chem.* 1999 (3):496-501).

TABLE 2

| Conjugate No. | Peptide Sequence |
| --- | --- |
| 1 | Ac-YDERYIG-polyLys |
|   | (core peptide disclosed as SEQ ID NO: 43) |
| 2 | Ac-RYDERYIG-polyLys |
|   | (core peptide disclosed as SEQ ID NO: 41) |
| 3 | Ac-NRYDERYIG-polyLys |
|   | (core peptide disclosed as SEQ ID NO: 44) |
| 4 | Ac-LNRYDERYIG-polyLys |
|   | (core peptide disclosed as SEQ ID NO: 45) |
| 5 | Ac-GLNRYDERYIG-polyLys |
|   | (core peptide disclosed as SEQ ID NO: 46) |

Carriers bearing immobilized peptides according to the present invention may be then used to prepare affinity gels for isolating the protective antibodies from the blood/sera of donors. Antibodies produced in this way may be used in the production of blood-derived, immunoglobulin therapeutic preparations specific against enterobacteria.

Carriers bearing immobilized peptides according to the present invention may also be used in the diagnosis of specific humoral immunity insufficiencies. Due to their specificity, the diagnostic tests containing peptides according to the present invention are particularly useful for determining the level of antibodies specific against important pathogens of the gastrointestinal tract, which have a great significance particularly in paediatrics.

EXAMPLE 9

Immunogenicity of the Synthesized Peptide Conjugates in a Mouse Model

Figure 6:
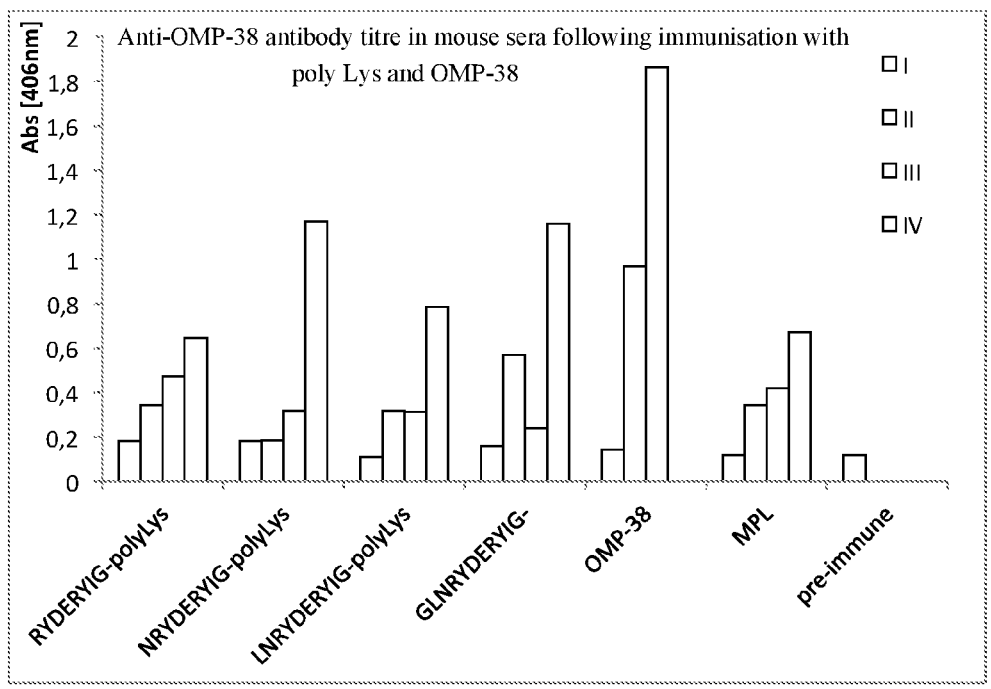

BALB/c mice were divided into 7 experimental groups, of which groups 1-4 received poly-lysine conjugates (gr. 1: RYDERYIG-polyLys (core peptide disclosed as SEQ ID NO: 41), gr. 2: NRYDERYIG-polyLys (core peptide disclosed as SEQ ID NO: 44), gr.3: LNRYDERYIG-polyLys (core peptide disclosed as SEQ ID NO: 45) and gr.4: GLNRYDERYIG-polyLys (core peptide disclosed as SEQ ID NO: 46)), group 5 received the OMP-38 protein, and the control groups received only the MPL adjuvant-gr. 6 or were not immunized at all—gr. 7. The mice were immunized intraperitoneally with a single dose of 200 μl of vaccine containing the appropriate antigen suspended in PBS with MPL adjuvant (5:1, vol/vol). The mice were immunized over 1.5 months at weekly intervals. After 7 days from each immunization, one mouse was bled from each group, and then the serum specific antibody level was ascertained which was evidence of an induced immune response using a standard ELISA test which measured the titre of antibodies directed against whole OMP-38 protein, wherein we determined the level of highly specific antibodies directed against the RYDERY epitope (SEQ ID NO: 2) present on the surface of OMP-38. The results are summarised in FIG. 6.

EXAMPLE 10

ELISA Test with Human Serum Facilitating the Rapid Detection of Differences in Anti-RYDERY (SEQ ID NO: 2) Antibody Concentrations in Patients' Sera Peptides with the same sequence (RYDERY (SEQ ID NO: 2)) were equilibrated in TBS-T buffer. Solid phase free space blocking was performed using a 1% BSA solution in TBS-T (1h, room temperature, 200 μl/well). We consecutively tested 100-fold of serum dilutions in TBS-T with 1% BSA (1h, room temperature, 100 μl/well). Next, the reactivity of antibodies present in the sera from patients were detected using anti-Human IgG conjugated with alkaline phosphatase (Sigma) at a dilution of 1:10000 (1h, room temperature, 100 μl/well), using pNPP (p-Nitrophenyl Phosphate, AP Yellow-Sigma) as a substrate.

The invention claimed is:

1. A conjugate comprising poly-Lys conjugated to a peptide of no more than twelve amino acids that comprises an amino-acid sequence selected from RYDERY (SEQ ID NO: 2), RYDDRY (SEQ ID NO: 3), RYEERY (SEQ ID NO: 4), RYQERY (SEQ ID NO: 5), and RYDQRY (SEQ ID NO: 6).

2. The conjugate of claim 1, wherein the peptide is selected from the group consisting of the peptides RYDERY (SEQ ID NO: 2), RYDDRY (SEQ ID NO: 3), RYEERY (SEQ ID NO: 4), RYQERY (SEQ ID NO: 5), and RYDQRY (SEQ ID NO: 6).

3. A method of inducing production of antibodies against the OMP-38 protein of *Shigella flexneri* 3a, comprising immunizing a host with the conjugate according to claim 1.

4. A method of inducing production of antibodies against the OMP-38 protein of *Shigella flexneri* 3a, comprising immunizing a host with the conjugate according to claim 2.

5. A method of making the conjugate according to claim 1, comprising conjugating the poly-Lys to the peptide.

6. A method of making the conjugate according to claim 2, comprising conjugating the poly-Lys to the peptide.

* * * * *

UNITED STATES PATENT AND TRADEMARK OFFICE
CERTIFICATE OF CORRECTION

PATENT NO. : 9,890,194 B2  
APPLICATION NO. : 14/441248  
DATED : February 13, 2018  
INVENTOR(S) : Anna Ewelina Jarząb et al.

Page 1 of 1

It is certified that error appears in the above-identified patent and that said Letters Patent is hereby corrected as shown below:

On the Title Page

Item (71):
"WROCLAWSKIE CENTRUM BADANEIT + SP. Z O.O.",
Should read:
--WROCLAWSKIE CENTRUM BADAN EIT + SP. Z O.O.--

Signed and Sealed this
Sixth Day of November, 2018

Andrei Iancu
*Director of the United States Patent and Trademark Office*

SEQUENCE LISTING

```
<160> NUMBER OF SEQ ID NOS: 75

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Asp, Arg, Glu, Asn or Gln
<220> FEATURE:
<221> NAME/KEY: MOD_RES
<222> LOCATION: (4)..(4)
<223> OTHER INFORMATION: Glu, Asp, Asn or Gln
<220> FEATURE:
<221> NAME/KEY: MOD_RES
```

```
<222> LOCATION: (6)..(6)
<223> OTHER INFORMATION: Tyr, Gly or Phe

<400> SEQUENCE: 1

Arg Tyr Xaa Xaa Arg Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Tyr Asp Glu Arg Tyr
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Tyr Asp Asp Arg Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Tyr Glu Glu Arg Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Tyr Gln Glu Arg Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Tyr Asp Gln Arg Tyr
1               5
```

```
<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Asn Ser Ala Glu Asn Glu Asn Asn Ser Trp Thr
1               5                   10

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Gly Glu Gly Met Thr Asn Asn Gly Arg Glu Ala Leu Arg Gln Asn
1               5                   10                  15

Gly Asp Gly Val
            20

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Leu Asn Arg Tyr Asp Glu Arg Tyr Ile Gly Asn
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Val Ile Asn Gly Arg Asn Thr Asp Asp Glu Asp
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Asp Asn Gln Phe Thr Arg Asp Ala Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 12

Ala Glu Val Tyr Asn Lys Asp Gly Asn Lys Leu Asp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Glu Thr Tyr Thr Gly Gly Leu Lys Tyr Asp
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Arg Ala Glu Thr Tyr Thr Gly Gly Leu Lys Tyr
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Asp Arg Ala Glu Thr Tyr Thr Gly Gly Leu Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Gly Asp Arg Ala Glu Thr Tyr Thr Gly Gly Leu
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Asn Gly Asp Arg Ala Glu Thr Tyr Thr Gly Gly
1               5                   10

<210> SEQ ID NO 18

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Gly Asn Gly Asp Arg Ala Glu Thr Tyr Thr Gly
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Ile Gly Asn Gly Asp Arg Ala Glu Thr Tyr Thr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Tyr Ile Gly Asn Gly Asp Arg Ala Glu Thr Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Arg Tyr Ile Gly Asn Gly Asp Arg Ala Glu Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Glu Arg Tyr Ile Gly Asn Gly Asp Arg Ala Glu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

Tyr Asp Glu Arg Tyr Ile Gly Asn Gly Asp Arg Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Tyr Asp Glu Arg Tyr Ile Gly Asn Gly Asp Arg
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Arg Tyr Asp Glu Arg Tyr Ile Gly Asn Gly Asp
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Asn Arg Tyr Asp Glu Arg Tyr Ile Gly Asn Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Gly Leu Asn Arg Tyr Asp Glu Arg Tyr Ile Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Phe Gly Leu Asn Arg Tyr Asp Glu Arg Tyr Ile
1               5                   10

<210> SEQ ID NO 29
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 29

Gln Asn Phe Gly Leu Asn Arg Tyr Asp Glu Arg Tyr
1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Gln Asn Phe Gly Leu Asn Arg Tyr Asp Glu Arg
1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Asp Gln Asn Phe Gly Leu Asn Arg Tyr Asp Glu
1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Asp Asp Gln Asn Phe Gly Leu Asn Arg Tyr Asp
1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Thr Asp Asp Gln Asn Phe Gly Leu Asn Arg Tyr
1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Arg Thr Asp Asp Gln Asn Phe Gly Leu Asn Arg
1               5                  10
```

```
<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Lys Arg Thr Asp Asp Gln Asn Phe Gly Leu Asn
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Ser Lys Arg Thr Asp Asp Gln Asn Phe Gly Leu
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ser Ser Lys Arg Thr Asp Asp Gln Asn Phe Gly
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Ser Ser Ser Lys Arg Thr Asp Asp Gln Asn Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Val Ser Ser Ser Lys Arg Thr Asp Asp Gln Asn
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

```
Ala Ala Val Ser Ser Ser Lys Arg Thr Asp Asp Gln
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Tyr Asp Glu Arg Tyr Ile Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Asp Glu Arg Tyr
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Tyr Asp Glu Arg Tyr Ile Gly
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asn Arg Tyr Asp Glu Arg Tyr Ile Gly
1               5

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Leu Asn Arg Tyr Asp Glu Arg Tyr Ile Gly
1               5                   10

<210> SEQ ID NO 46
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 46

Gly Leu Asn Arg Tyr Asp Glu Arg Tyr Ile Gly
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Glu Val Tyr Asn Lys Asp Gly Asn Lys Leu Asp Leu
1               5                   10

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Asp Lys Ser Val Asp Gly Asp
1               5

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Thr Gln Ile Asn Asp Gln Leu Thr Gly
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Glu Phe Lys Gly Asn Ser Ala Glu Asn Glu Asn Asn Ser Trp Thr
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Lys Asn Gly Ser Pro Glu Gly Glu Gly Met Thr Asn Asn Gly Arg
1               5                   10                  15
```

Glu Ala Leu Arg Gln Asn Gly Asp Gly Val Gly Gly Ser Ile Thr Tyr
            20                  25                  30

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Leu Asn Arg Tyr Asp Glu Arg Tyr Ile Gly Asn
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Gly Val Ile Asn Gly Arg Asn Thr Asp Asp Glu Asp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Asp, Arg, Glu, Asn or Gln
<220> FEATURE:
<221> NAME/KEY: MOD_RES
<222> LOCATION: (8)..(8)
<223> OTHER INFORMATION: Glu, Asp, Asn or Gln
<220> FEATURE:
<221> NAME/KEY: MOD_RES
<222> LOCATION: (10)..(10)
<223> OTHER INFORMATION: Tyr, Gly or Phe
<220> FEATURE:
<221> NAME/KEY: MOD_RES
<222> LOCATION: (11)..(11)
<223> OTHER INFORMATION: Ile or Gly

<400> SEQUENCE: 54

Phe Gly Leu Asn Arg Tyr Xaa Xaa Arg Xaa Xaa Gly
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Tyr Asp Glu Arg Gly
1               5

<210> SEQ ID NO 56
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 56

Arg Tyr Asp Glu Gly Tyr
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Tyr Asp Gly Arg Tyr
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Tyr Gly Glu Arg Tyr
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Arg Gly Asp Glu Arg Tyr
1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Tyr Asp Glu Arg Tyr
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Arg Phe Asp Glu Arg Tyr
1               5
```

```
<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Thr Asp Glu Arg Tyr
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Asp Glu Arg Tyr
1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Tyr Asp Glu Arg Phe
1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Tyr Asp Glu Arg Thr
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Tyr Asp Glu Arg Ser
1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 67

Leu Tyr Asp Glu Arg Tyr
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Tyr Asp Glu Leu Tyr
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Tyr Asp Glu Leu Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Tyr Asp Glu Arg Tyr
1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Tyr Arg Glu Arg Tyr
1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Tyr Gln Gln Arg Tyr
1               5

<210> SEQ ID NO 73
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Tyr Asp Glu Arg Tyr
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Tyr Asp Glu Lys Tyr
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Tyr Asp Glu Lys Tyr
1               5
```